(12) United States Patent
McGuckin, Jr. et al.

(10) Patent No.: US 9,668,848 B2
(45) Date of Patent: Jun. 6, 2017

(54) METHOD OF INSERTING A VEIN FILTER

(75) Inventors: James F. McGuckin, Jr., Radnor, PA (US); James Erich Bressler, Langhorne, PA (US); David M. Schaller, Wallingford, PA (US)

(73) Assignee: Argon Medical Devices, Inc., Plano, TN (US)

( * ) Notice: Subject to any disclaimer, the term of this patent is extended or adjusted under 35 U.S.C. 154(b) by 180 days.

(21) Appl. No.: 12/288,217

(22) Filed: Oct. 17, 2008

(65) Prior Publication Data
US 2009/0143813 A1 Jun. 4, 2009

Related U.S. Application Data

(60) Provisional application No. 61/001,665, filed on Nov. 2, 2007, provisional application No. 61/010,838, filed on Jan. 11, 2008.

(51) Int. Cl.
*A61F 2/01* (2006.01)

(52) U.S. Cl.
CPC ........... *A61F 2/01* (2013.01); *A61F 2002/011* (2013.01); *A61F 2250/0029* (2013.01)

(58) Field of Classification Search
CPC ...................... A61F 2002/011; A61M 25/0152
USPC ................. 606/108, 200; 623/1.11
See application file for complete search history.

(56) References Cited

U.S. PATENT DOCUMENTS

| | | | |
|---|---|---|---|
| 4,020,829 A | 5/1977 | Willson et al. | |
| 4,758,222 A | 7/1988 | McCoy | |
| 4,790,331 A | 12/1988 | Okada et al. | |
| 4,819,634 A | 4/1989 | Shiber | |
| 4,832,055 A * | 5/1989 | Palestrant | 128/899 |
| 4,983,169 A | 1/1991 | Furukama | |
| 5,109,830 A | 5/1992 | Cho | |
| 5,231,989 A | 8/1993 | Middleman | |
| 5,246,420 A | 9/1993 | Kraus et al. | |
| 5,345,937 A * | 9/1994 | Middleman et al. | 604/95.01 |
| 5,601,568 A | 2/1997 | Chevillon et al. | |
| 5,630,801 A * | 5/1997 | Roussigne et al. | 606/108 |
| 6,011,988 A | 1/2000 | Lynch | |
| 6,074,361 A | 6/2000 | Jacobs | |
| 6,126,673 A | 10/2000 | Kim et al. | |
| 6,231,589 B1 | 5/2001 | Wessman et al. | |
| 6,231,989 B1 | 5/2001 | Chung et al. | |
| 6,235,000 B1 | 5/2001 | Milo | |
| 6,267,776 B1 * | 7/2001 | O'Connell | 606/200 |
| 6,447,522 B2 | 9/2002 | Gambale et al. | |
| 6,506,205 B2 | 1/2003 | Goldberg | |
| 6,572,593 B1 | 6/2003 | Daum | |
| 6,592,559 B1 | 7/2003 | Pakter | |
| 6,632,184 B1 | 10/2003 | Truwit | |

(Continued)

FOREIGN PATENT DOCUMENTS

WO    WO-02/102436    12/2002

*Primary Examiner* — Sarah W Aleman
(74) *Attorney, Agent, or Firm* — IpHorgan Ltd.

(57) ABSTRACT

A method of implanting a vessel filter by a femoral approach comprising the steps of providing a delivery sheath with a substantially straight distal tip and inserting a curved device into the sheath to move the sheath to a second configuration. In the second position, the distal tip of the sheath is curved at an angle to a longitudinal axis of the sheath. The method further comprises the step of rotating the sheath and pusher so a distal opening of the sheath has a more centered position within the vessel.

12 Claims, 4 Drawing Sheets

(56) References Cited

U.S. PATENT DOCUMENTS

| | | |
|---|---|---|
| 6,783,538 B2 | 8/2004 | McGuckin, Jr. et al. |
| 6,793,665 B2 | 9/2004 | McGuckin, Jr. et al. |
| 6,890,340 B2 | 5/2005 | Duane |
| 6,932,831 B2 | 8/2005 | Forber |
| 6,958,074 B2 | 10/2005 | Russell |
| 6,972,025 B2 | 12/2005 | WasDyke |
| 6,989,021 B2 | 1/2006 | Bosma et al. |
| 6,994,092 B2 | 2/2006 | Van de Burg et al. |
| 7,037,321 B2 | 5/2006 | Sachdeva et al. |
| 7,097,651 B2 | 8/2006 | Harrison et al. |
| 7,338,512 B2 | 3/2008 | McGuckin, Jr. et al. |
| 2002/0156452 A1 | 10/2002 | Pursley |
| 2002/0193828 A1 | 12/2002 | Griffin et al. |
| 2004/0054322 A1 | 3/2004 | Vargas |
| 2004/0181150 A1 | 9/2004 | Evans |
| 2005/0004555 A1 | 1/2005 | Pursley |
| 2005/0015007 A1 | 1/2005 | Itou |
| 2005/0075625 A1 | 4/2005 | Dao |
| 2005/0165442 A1 | 7/2005 | Thinnes et al. |
| 2005/0256375 A1 | 11/2005 | Freed |
| 2006/0079928 A1 | 4/2006 | Cartier et al. |
| 2006/0079930 A1 | 4/2006 | McGuckin, Jr. et al. |
| 2006/0135915 A1 | 6/2006 | Tucker |
| 2006/0135916 A1 | 6/2006 | Tucker |
| 2006/0282043 A1 | 12/2006 | Pyles |
| 2007/0088381 A1 | 4/2007 | McGuckin, Jr. et al. |
| 2007/0213685 A1 | 9/2007 | Bressler et al. |
| 2008/0188887 A1 | 8/2008 | Batiste |
| 2008/0221609 A1 | 9/2008 | McGuckin, Jr. et al. |
| 2008/0275486 A1 | 11/2008 | Dwyer et al. |
| 2009/0198270 A1 | 8/2009 | McGuckin, Jr. |

\* cited by examiner

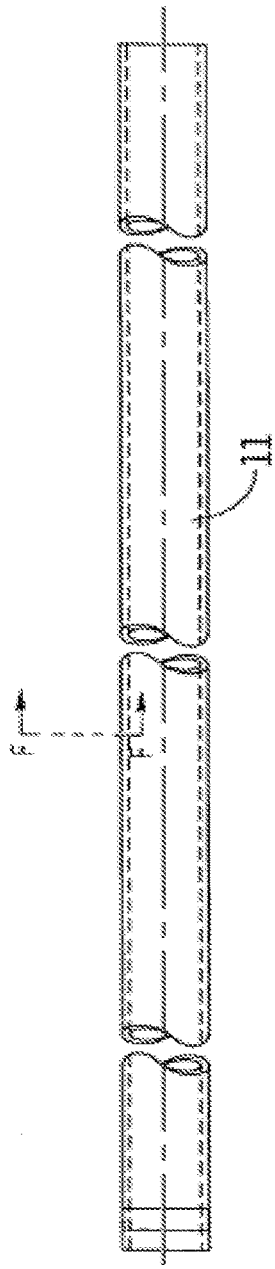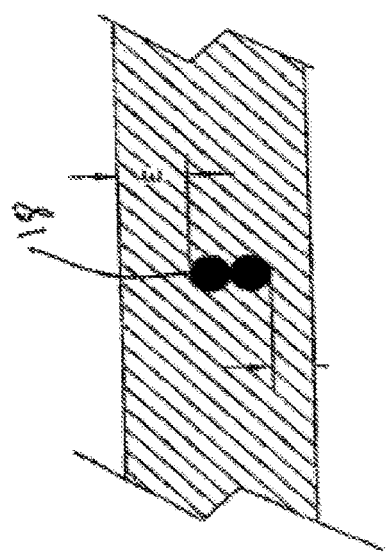

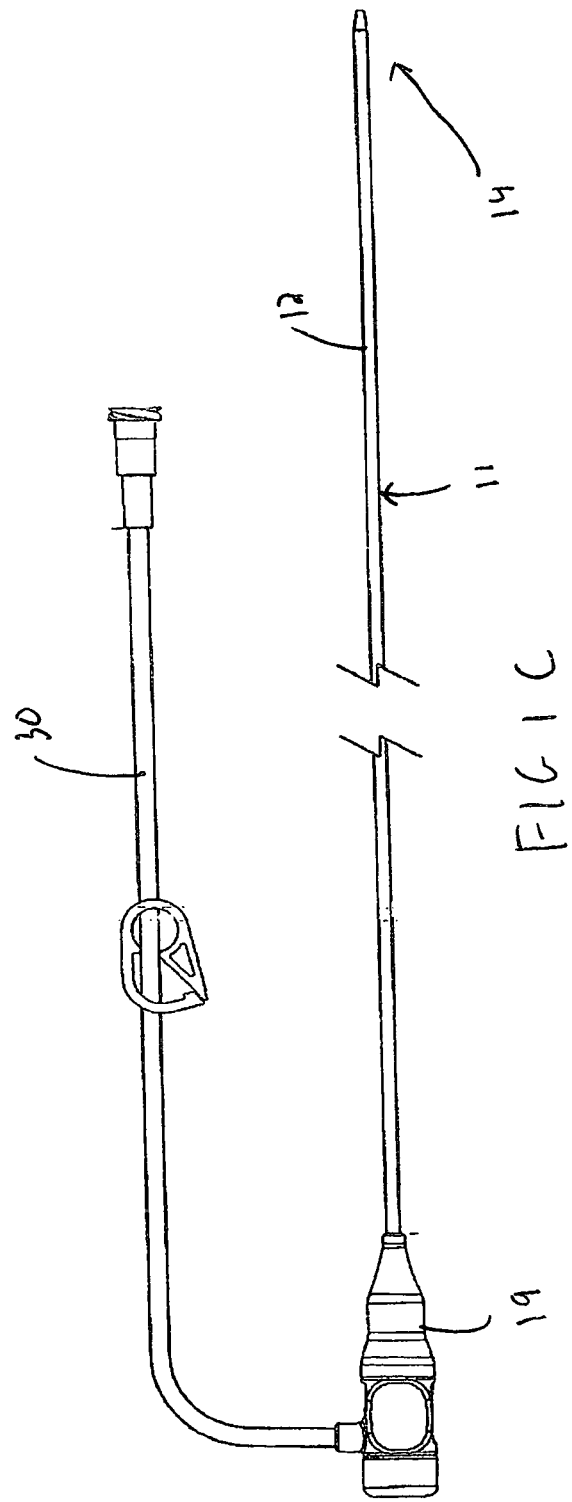

FIG_2
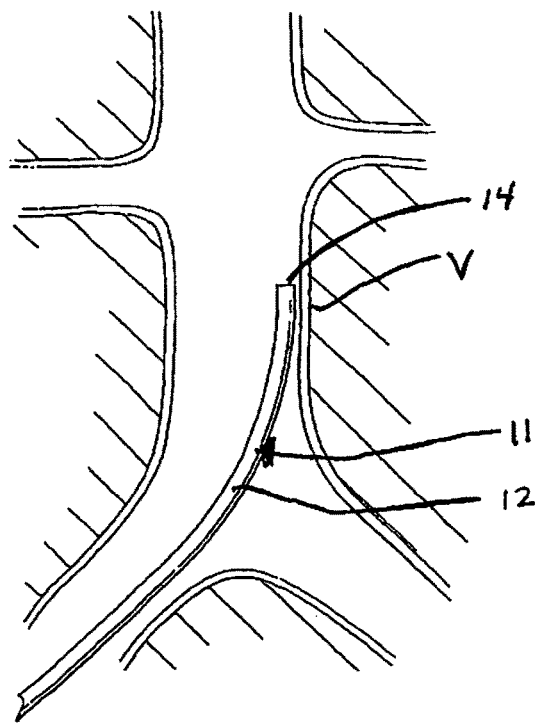
FIG_3
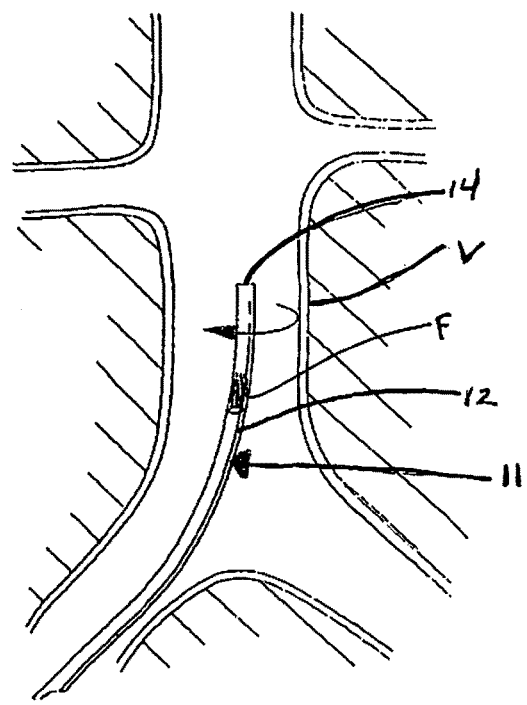

METHOD OF INSERTING A VEIN FILTER

This application claims priority from provisional application Ser. No. 61/001,665, filed Nov. 2, 2007 and from provisional application Ser. No. 61/010,838, filed Jan. 11, 2008. The entire contents of each of these applications is incorporated herein by reference.

BACKGROUND

Technical Field

This application relates to a vascular filter and more particularly to a method of inserting a vein filter into the vessel.

Background of Related Art

Passage of blood clots to the lungs is known as pulmonary embolism. These clots typically originate in the veins of the lower limbs and can migrate through the vascular system to the lungs where they can obstruct blood flow and therefore interfere with oxygenation of the blood. Pulmonary embolisms can also cause shock and even death.

In some instances, blood thinning medication, e.g. anticoagulants such as Heparin, or sodium warfarin can be given to the patient. These medications, however, have limited use since they may not be able to be administered to patients after surgery or stroke or given to patients with high risk of internal bleeding. Also, this medication approach is not always effective in preventing recurring blood clots.

To avoid invasive surgery, less invasive surgical techniques involving placement of a mechanical barrier in the inferior vena cava have been developed. These barriers are in the form of filters and are typically inserted through either the femoral vein in the patient's leg or the right jugular vein in the patient's neck or arm under local anesthesia. The filters are then advanced intravascularly to the inferior vena cava where they are expanded to block migration of the blood clots from the lower portion of the body to the heart and lungs.

These prior filters take various forms. One type of filter is composed of coiled wires such as disclosed in U.S. Pat. Nos. 5,893,869 and 6,059,825. Another type of filter consists of legs with free ends having anchors for embedding in the vessel wall to hold the filter. These filters are disclosed, for example, in U.S. Pat. Nos. 4,688,553, 4,781,173, 4,832,055, and 5,059,205, 5,984,947 and 6,007,558. Another type of filter is disclosed in U.S. Pat. No. 6,214,025 consisting of wires twisted together to form a cylindrical anchoring portion conforming to the inner vessel wall surface to exert a radial force and a conical filtering portion.

Co-pending commonly assigned U.S. application Ser. No. 10/899,429 (the "'429 application"), the entire contents of which is incorporated herein by reference, discloses other forms of vein filters. These filters can be permanently implanted or removed minimally invasively, e.g. intravascularly.

The methods of placement of the filter described in the '429 are effective. However, in certain patients, the vena cava is not straight, but is curved and/or more tortuous. Although the filters of the '429 application can be placed effectively in such vena cava, it would be advantageous to provide a delivery method and apparatus to even better accommodate these curved anatomies.

Additionally, the better centered the filter, the easier the subsequent removal of the filter. This is due to the fact that if the caudal end (the proximal retrieval end) of the filter is against the vessel wall when placed, access to the retrieval end could be difficult. Also, additional tissue ingrowth could occur over the proximal end which could increase the difficulty of removal. Therefore, it would be advantageous to provide a filter delivery system which could improve centered delivery of the filter.

SUMMARY

The present invention provides a method of implanting a filter to facilitate centering of filter at the surgical site. The present invention also provides a method of delivering the filter in a manner to facilitate later removal of the filter from the vessel. This is achieved by providing a pusher with a curved distal portion which in turn curves the delivery sheath. Therefore, if the delivery sheath, due to the curved anatomy is delivered against the wall of the vessel, the clinician can rotate the sheath and pusher from a proximal portion to move it away from the vessel wall so the distal opening of the sheath is more centered.

In one aspect, the present invention provides a method of implanting a vessel filter by a femoral approach comprising the steps of providing a sheath with a substantially straight distal tip, inserting a curved device into the sheath to move the sheath to a curved position from a more straightened position, rotating the sheath and curved device to move a distal opening of the sheath to a more centered position within the vessel, and exposing a filter contained within the sheath.

The curved device preferably has a curved distal tip and the step of inserting the curved device preferably curves a distal portion of the sheath, leaving the remaining portions substantially straight.

In a preferred embodiment, the sheath has at least a first portion of a first hardness or stiffness and the curved device has at least a second portion of a second hardness or stiffness to cause the sheath tip to curve. The second hardness is preferably at the distal end of the curved device and the first hardness is preferably at the distal end of the sheath, such that in the step of inserting the curved device, the second hardness causes the sheath distal end to move to a more curved position The present invention also provides an implantation system for a vascular implant comprising a sheath having a longitudinal axis, a lumen formed therein and a distal opening, wherein the sheath has a normally substantially straight configuration. The implant is positioned within the lumen of the sheath and configured for deployment through the distal opening in the sheath for implantation in a patient's body. A pusher is slidably positioned with respect to the sheath, the pusher having a curved distal portion, wherein positioning of the curved distal portion of the pusher at a distal portion of the sheath moves the distal portion of the sheath from the substantially straight configuration to a curved position at an angle to a longitudinal axis of the sheath.

In one embodiment, the pusher comprises an extrusion with a metal wire positioned therein. Preferably, the pusher comprises a hub at the proximal end, wherein rotation of the hub rotates the distal end of the pusher. One type of implant which can be delivered using the implantation system is a vessel filter with vessel engaging hooks and which can move to an expanded configuration when deployed from the sheath. In one embodiment, the pusher advances the implant from a proximal end of the sheath to a distal end.

The present invention also provides in combination, a delivery sheath, a filter and a pusher. The delivery sheath has a lumen therein dimensioned to receive the filter and the sheath has a normally substantially straight configuration.

The filter is positioned within the sheath and configured for deployment through a distal opening in the sheath for implantation in a patient's body. The pusher is slidably positioned with respect to the sheath, and has a curved tip and is engagable with the filter for advancement of the filter within the lumen of the sheath. The pusher is positionable in the sheath such that the curved tip moves a distal portion of the sheath from a substantially straight position to a curved position at an angle to a longitudinal axis of the sheath.

In one embodiment, the pusher advances the filter from a proximal end of the sheath to a distal end.

BRIEF DESCRIPTION OF THE DRAWINGS

Preferred embodiment(s) of the present disclosure are described herein with reference to the drawings wherein:

FIG. 1A is a side view of the delivery sheath in the straightened position;

FIG. 1B is a cross-sectional view taken along line F-F of FIG. 1A;

FIG. 1C is a side view of the filter delivery system showing the delivery sheath in the normal straightened position;

FIG. 2 illustrates the delivery sheath inserted via a femoral approach and in contact with a wall of the vessel; and FIG. 3 illustrates the delivery sheath (and pusher) rotated to better center the opening of the sheath within the vessel for delivery of the filter.

DETAILED DESCRIPTION OF PREFERRED EMBODIMENTS

Figure 1:
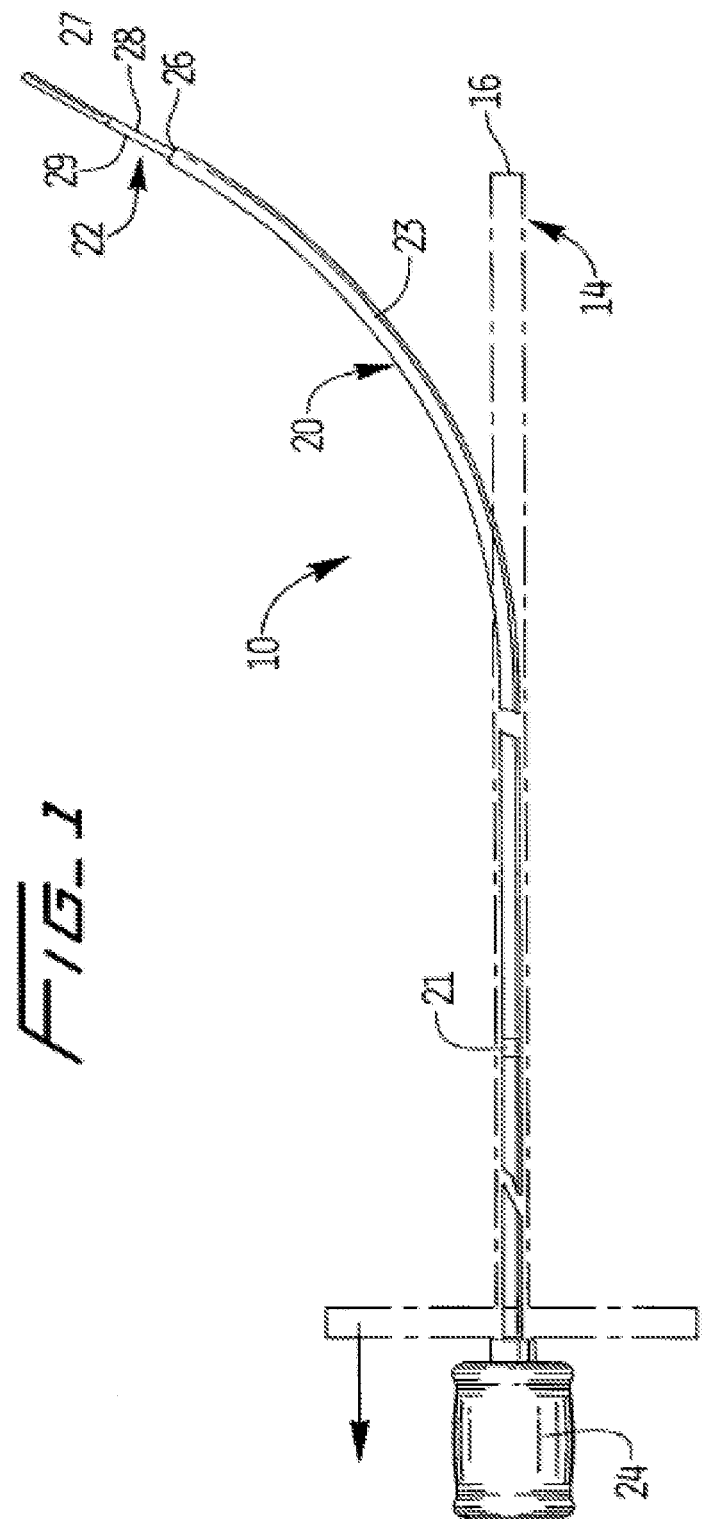
FIG. 1 is a side view of the delivery sheath shown in the curved position and in phantom in the straightened position.

Turning now to the drawings, wherein like reference numerals identify similar or like components throughout the several views, a method of implanting vein filters is disclosed. The filter is inserted via a femoral approach. In co-pending commonly assigned patent application Ser. No. 10/899,429 (hereinafter the "'429 application"), filed Jul. 12, 2004, the entire contents of which are incorporated herein by reference, various embodiments of filters are described with various structures. The delivery system of the present invention can be used to insert filters of the '429 application as well as used to insert other filters.

As is common, the term "proximal" used herein refers to the part closer to the user, e.g. surgeon, and the term "distal" refers to the part further from the user.

Turning initially to FIG. 1 and FIG. 1C, the filter delivery system 10 of the present invention has a sheath 11 having a body 12, a distal tip 14 and a distal opening 16. The distal tip 14 in its normal position is substantially straight and substantially aligned with the longitudinal axis of the sheath. This configuration is shown in FIG. 1C and in phantom in FIG. 1.

The filter pusher is designated by reference numeral 20 and has a curved tip 22, hub 24 and body 23. When inserted through the sheath 11 after placement of the sheath in the vena cava (and removal of the dilator from the sheath), the curved tip 22 at the distal portion of pusher 20 causes the distal tip 14 of sheath 11 to curve from the substantially straight configuration of FIG. 1 (shown in phantom) to the curved configuration shown in FIG. 1. That is, the sheath 11 would take the form of the curved pusher 20 of FIG. 1. The catheter tip 14 is sufficiently flexible to be curved by insertion of pusher (or curved device) 20 through the lumen of the sheath. The remaining portions of sheath 11 remain substantially straight as shown.

In a preferred embodiment, the pusher 20 is formed of Pebax material which is insert molded over a guidewire 27, preferably composed of stainless steel. This wire core 27 (FIG. 1) provides increased stiffness to the pusher 20 to facilitate bending of the catheter tip 14. Other materials and compositions of the pusher are contemplated, provided it has the requisite stiffness to bend the distal portion of the catheter as described herein. The wire 27 is seen protruding from the Pebax body 23 of the pusher 20. A metal ferrule 28 is shown at the distalmost end 26 of the pusher body, attached to the guidewire 27, over which the filter hooks are positioned to keep them separated during insertion. A marker band 21 or other indicia provides a visual indication of when the filter is at the distal end of the sheath (when the markings are adjacent a proximal end of a filter cartridge).

In a preferred embodiment, the sheath 11 is composed of a Pebax material with a stainless steel braid 18 (see FIG. 1B) embedded in the wall to increase its rigidity. A PTFE liner or coating is preferably provided on the inner surface of the sheath. Other materials and compositions are also contemplated. The sheath hub is designated by reference numeral 19 (FIG. 1C). Tubing 30 allows for injection of cold saline as described in the '429 application which can be provided to maintain the filter in a relatively softer condition as it is in the martensitic state within the sheath.

The sheath 11 preferably has a first stiffness (or hardness) and the curved pusher 20 preferably as a second stiffness (or hardness) greater than the first stiffness (hardness) of the sheath 11 to cause the sheath tip to curve. This different stiffness could be throughout the sheath and pusher, or alternately could be only in portion, provided it is in a distal enough portion to cause the distal tip of the sheath 11 to move to its curved position. It is also contemplated that the stiffnesses could be about the same, since even if of substantially equal stiffness, the curve of the pusher could be sufficient to cause a bend in the catheter tip.

During one method of manufacture, the pusher is extruded in a straight configuration and then wrapped around a cylinder and heated to form a curve. The pusher can be "overcurved" during manufacture to ensure bending of the catheter.

In use, once the sheath and dilator are inserted through the femoral vein and advanced through the iliac vein into the inferior vena cava, the dilator is removed. Due to the anatomy of the particular patient's vena cava, the sheath 11 may end up against the vessel wall V such that distal opening is close to the vessel wall (see FIG. 2). If the filter (not shown) was then delivered by the sheath, it would not be centered on delivery. Consequently, in accordance with the present invention, the next step of insertion if the distal tip of sheath 11 is tangent to the vessel wall V is to rotate the sheath 11 and pusher 20 from a proximal end, causing them to rotate so the distal opening 14 of sheath 11 is rotated away from the vessel and is more centered in the vessel, thus better ensuring the filter will be initially placed in a more centered position.

After exposure of the filter F by advancing the pusher to eject the filter F or retracting the sheath with the pusher held stationary, or relative movement of both the pusher and sheath, the pusher and sheath are removed, enabling the filter to expand and leaving the filter in place in the vena cava as described in the '429 application.

If it is later desired to remove the filter, the retrieval methods for the filter which are illustrated and described in detail in the '429 application, such as a retrieval snare, can be utilized.

If the filter is more centered in the vessel, the retrieval snare is better adapted to access and engage (grasp) the retrieval hook of the filter. Also, if placement is more centered, removal can be easier because there will be less tissue ingrowth at the retrieval hook region.

Although described for inserting a vessel filter, the pusher and sheath can be utilized to insert other implants such as a stent, a valve and other vascular devices.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A method of implanting a vessel filter by a femoral approach comprising the steps of:
   providing a sheath with a substantially straight distal tip;
   providing a curved pusher with a wire fixedly attached therein, a distal portion of the wire extending distally beyond a distal portion of the curved pusher;
   inserting the curved pusher and attached wire together into the sheath, the step of inserting both moving the sheath to a curved position from a more straightened position and contacting and advancing the vessel filter in the sheath, the pusher having a distal portion extendable distal of the sheath;
   rotating about a longitudinal axis of the sheath, the sheath and curved pusher to move a distal opening of the sheath to a more centered position within the vessel; and
   exposing a filter contained within the sheath by advancing the curved pusher and attached wire together within the sheath, by retracting the sheath from the curved pusher and attached wire, or by relative movement between the sheath and the curved pusher and attached wire.

2. The method of claim 1, further comprising the step of advancing the sheath through the femoral vein into the vena cava.

3. The method of claim 1, wherein at least a portion of the sheath has a first hardness and at least a portion of the curved pusher has a second hardness greater than the first hardness to move the sheath to a more curved position when the curved pusher is inserted into the sheath.

4. The method of claim 1, wherein the step of rotating the sheath and curved pusher comprises the step of rotating the sheath and curved pusher from a proximal end portion.

5. The method of claim 4, wherein the step of rotating the sheath and curved pusher moves a distal opening of the sheath from a position tangent to a vessel wall.

6. The method of claim 1, further comprising the step of advancing the curved pusher to push the filter through the sheath.

7. The method of claim 1, wherein the curved pusher has a curved distal tip and the step of inserting the curved pusher curves a distal portion of the sheath, leaving the remaining portions of the sheath substantially straight.

8. The method of claim 1, wherein the wire is a metal wire.

9. The method of claim 8, wherein the pusher includes a ferrule positioned at a distal end.

10. The method of claim 1, wherein the wire extends through a series of hooks of the filter during the insertion step.

11. The method of claim 1, wherein the pusher comprises an extrusion with the wire attached therein composed of metal.

12. The method of claim 11, wherein the metal wire is positioned distal of the sheath during implanting the filter.

* * * * *